United States Patent [19]

West et al.

[11] Patent Number: 4,692,457

[45] Date of Patent: Sep. 8, 1987

[54] ACARICIDES

[75] Inventors: Peter J. West, Great Shelford; Russell G. Hunt, Burwell; Duncan A. Gates, Littlebury, all of England

[73] Assignee: FBC Limited, England

[21] Appl. No.: 852,181

[22] Filed: Apr. 15, 1986

[30] Foreign Application Priority Data

Apr. 16, 1985 [GB] United Kingdom ............... 85/09752

[51] Int. Cl.⁴ .................... C07D 285/08; A01N 47/18
[52] U.S. Cl. .................................... 514/361; 548/129; 548/130
[58] Field of Search ................. 548/130, 129; 514/361

[56] References Cited

U.S. PATENT DOCUMENTS 3,917,630 11/1975 Hambook ............................ 548/129

FOREIGN PATENT DOCUMENTS 25382 11/1963 Japan ................................... 548/129

OTHER PUBLICATIONS

March, Advanced Organic Chemistry, 2nd ed., pp. 812, 813 (1979).

Primary Examiner—Robert Gerstl
Attorney, Agent, or Firm—Ostrolenk, Faber, Gerb & Soffen

[57] ABSTRACT

The invention provides the acaricidal thiadiazoles of the formula:

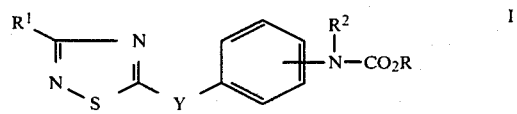

(where: $R^1$ and $R^2$, which may be the same or different, are each hydrogen, optionally-substituted alkyl of 1 to 10 carbon atoms, or optionally-substituted phenyl, of $R^1$ is alkylthio of 1 to 6 carbon atoms; R is an ester-forming group; Y is oxygen or sulphur; and the carbamate grouping is in the 3- or 4-position on the phenyl ring), processes for their preparation and compositions containing them.

13 Claims, No Drawings

ACARICIDES

This invention concerns acaricidal thiadiazoles, processes for their preparation, and compositions containing them.

In one aspect, the invention provides the thiadiazoles of the formula:

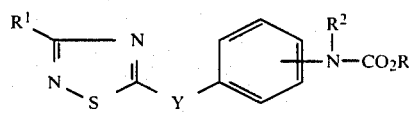

where: $R^1$ and $R^2$, which may be the same or different, are each hydrogen, optionally-substituted alkyl of 1 to 10 carbon atoms, or optionally-substituted phenyl, or $R^1$ is alkylthio of 1 to 6 carbon atoms: R is an ester-forming group; Y is oxygen or sulphur: and the carbamate grouping is in the 3- or 4-position on the phenyl ring.

When $R^1$ or $R^2$ represents alkyl, it is preferably of 1 to 6, especially of 1 to 4, carbon atoms, for example methyl, ethyl, n-propyl, isopropyl, n-butyl or t-butyl, and is desirably unsubstituted.

$R^1$ is preferably alkyl or alkylthio of 1 to 3 carbon atoms, or phenyl, specifically preferred groups being ethyl, n-propyl, isopropyl, ethylthio and phenyl.

$R^2$ is preferably hydrogen.

The ester-forming group which R represents may be any suitable such group, but is preferably a substituted or unsubstituted alkyl group of 1 to 8 carbon atoms, a substituted or unsubstituted alkenyl or alkynyl group of 2 to 6 carbon atoms, a cycloalkyl group of 3 to 6 carbon atoms, or a substituted or unsubstituted aryl group. It is particularly preferred that R represents phenyl, an alkyl group, desirably of 1 to 4 carbon atoms, which is preferably unsubstituted, or a cycloalkyl group. When the group R represents an alkenyl group, it is preferably vinyl or allyl, and when it represents an alkynyl group it is preferably 1,1-dimethylpropargyl.

Particularly preferred groups which R may represent include methyl, ethyl, n-propyl, isopropyl, n-butyl, sec-butyl, t-butyl, cyclopropyl, 1-methylhepthyl, phenyl, α-methylbenzyl, and a-isopropylbenzyl.

When any of the groups R, $R^1$ and $R^2$ is substituted, it may be substituted for example by one or more halogen atoms, eg chlorine or bromine, or alkoxy groups of 1 to 4 carbon atoms.

Y is preferably oxygen.

The carbamate group is preferably attached to the phenyl ring in the 3-position.

In a particularly preferred group of compounds according to the invention, $R^1$ is ethyl, n-propyl, isopropyl, ethylthio or phenyl, $R^2$ is hydrogen, Y is oxygen, R is methyl, ethyl, n-propyl, isopropyl, n-butyl, isobutyl, sec-butyl, t-butyl, cyclopropyl, 1-methylheptyl, phenyl, α-methylbenzyl or α-isopropylbenzyl, and the carbamate group is attached to the phenyl ring in the 3-position.

Specific preferred compounds of the invention are those of the Examples provided hereinafter. Particular mention may be made however of the compound [3-(3-n-propyl-1,2,4-thiadiazol-5-yloxy)phenyl]carbamate.

In another aspect, the invention provides a process for the preparation of a thiadiazole of formula I, in which a compound of the formula:

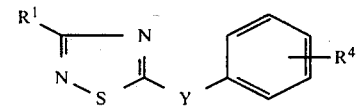

where $R^1$ and Y are as defined hereinbefore and $R^4$ represents —NCO or —$NR^2$. COCl and is in the 3- or 4-position on the phenyl ring, is reacted with an alcohol of the formula ROH where R is as defined hereinbefore, to give the desired compound.

The reaction is conveniently effected by heating the isocyanate to a temperature of from 30° to 150° C. with a molar excess of the alcohol, preferably under reflux.

The compounds of formula II may themselves be prepared by reacting the corresponding amines of the formula:

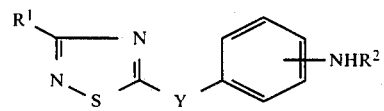

where $R^1$, $R^2$ and Y are as defined hereinbefore, with phosgene in a suitable solvent medium to give the desired compound.

The reaction is preferably effected in an aromatic solvent which is a good solvent for the phosgene but does not react therewith, for example an aromatic hydrocarbon, eg toluene. The phosgene is desirably dissolved in the solvent prior to reaction with the amine, which is conveniently effected with heating to a temperature of from 30° to 150° C. and preferably under reflux.

Where $R^2$ in the compound of formula III is hydrogen, the compound of formula II produced is one in which $R^4$ represents —NCO. Where $R^2$ in the compound of formula III is other than hydrogen, the compound of formula II produced is one in which $R^4$ represents —$NR^2$. COCl.

In turn, the amines of formula III may be prepared by reaction of a thiadiazolyl halide of the formula:

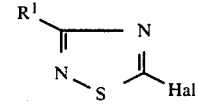

where $R^1$ is as defined hereinbefore, and Hal represents halogen, is reacted in the presence of a base with a phenylamine of the formula:

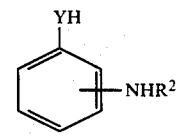

where $R^2$ and Y are as defined hereinbefore and the amino group is in the 3- or 4-position on the phenyl ring to give the desired compound.

The base employed is preferably a strong base, e.g. sodium hydride, and the reaction is conveniently effected in a suitable inert solvent medium, for example dimethylformamide or tetrahydrofuran.

The thiadiazoles of formula I in which $R^2$ is other than hydrogen may be prepared by conventional alkylation processes from the corresponding compounds where $R^2$ is hydrogen.

The compounds of formula I may alternatively be prepared by reaction in the presence of a base of a phenylcarbamate of the formula:

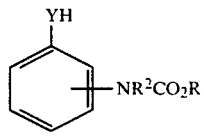

VI where R, $R^2$ and Y are as defined hereinbefore, and the carbamate group is in the 3- or 4- position on the phenyl ring, with a thiadiazolyl halide of formula IV as defined hereinbefore.

The base employed is preferably a strong base, e.g. sodium hydride, and the reaction is conveniently effected in a suitable inert solvent medium, for example dimethylformamide or tetrahydrofuran.

The compounds of formula VI may themselves be prepared by reaction of the appropriate aminophenol with a chloroformate of the formula $ClCO_2R$ by methods known per se.

The thiadiazoles of formula I are of particular use against the eggs and larvae of acarids, particularly the eggs of the red spider mite, *Tetranychus cinnabarinus*, but also against the eggs and larvae of other mite species, e.g. *Tetranychus urticae, Panonychus ulmi, Phyllocoptruta oleivora, Eutetranychus banksi, Panonychus citri* and *Tetranychus Mcdanieli*.

Many of the compounds of the invention possess vapour phase activity, which is a particular benefit where direct contact with the acarids, their eggs or their larvae is difficult to achieve.

The compounds of the invention are normally employed in the form of compositions, which normally contain from 0.5 to 99%, preferably from 0.5 to 85% by weight, more usually from 10 to 50% by weight, of the active compounds. These are diluted if necessary before application to the locus to be treated such that the concentration of active ingredient in the formulation applied is from 0.05 to 5% by weight.

The thiadiazoles of formula I are generally water insoluble and may be formulated in any of the ways commonly adopted for insoluble compounds.

For example, they may be dissolved in a water immiscible solvent, for example a high boiling hydrocarbon, as carrier, suitably containing dissolved emulsifying agents so that the composition acts as a self-emulsifiable oil on addition to water.

The thiadiazoles may alternatively be admixed with a wetting agent with or without a solid carrier to form a wettable powder which is soluble or dispersible in water, or may be mixed with just a solid carrier to form a solid product.

An aqueous suspension concentrate may alternatively be prepared by grinding the compounds with water, a wetting agent and a suspending agent.

Solid carriers with which the substituted thiadiazoles may be incorporated include clays, sands, talc, mica or solid fertilizers, such products either comprising dust or larger particle size materials.

The surface active agents used may comprise anionic surface active agents, for example mono- or di-esters of phosphoric acid with fatty alcohol ethoxylates or salts of such esters, fatty alcohol sulphates, ethoxylated alkylphenol sulphates, lignin sulphonates, petroleum sulphonates, alkylaryl sulphonates such as alkyl-benzene sulphonates or lower alkyl-naphthalene sulphonates, salts of sulphonated naphthalene-formaldehyde condensates, salts of sulphonated phenol-formaldehyde condensates, or more complex sulphonates such as the amide sulphonates, e.g. the sulphonated condensation product of oleic acid and N-methyl taurine or the dialkyl sulphosuccinates e.g. the sodium sulphonates of dioctyl succinate.

The surface active agents may also comprise nonionic agents, for example condensation products of fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acethylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, sodium oleoyl N-methyltauride, dialkyl sulphosuccinates, alkyl phenol ethoxylates, and fatty alkyl ethoxylates.

The composition may alternatively be in the form of an aerosol composition, suitably using a cosolvent and a wetting agent, in addition to the propellant, which is suitably a polyhalogenated alkane such as dichlorodifluoromethane.

The compositions according to the present invention may contain in addition to the substituted thiadiazoles other active insecticides, acaricides, ovicides, bactericides and fungicides. It has been found that particular advantages are obtained with mixture with other acaricides, e.g. clofentezine, but especially those which combat the adult stages, e.g. amitraz, dicofol, cyhexatin or propargite, and particularly where the compound of formula I is one of those exemplified herein, especially isopropyl [3-(3-n-propyl-1,2,4-thiadiazol-5-yloxy)-phenyl]carbamate.

The method of combating acarids, their eggs or their larvae provided by the present invention may be employed at any site where infestations of such pests are present or are liable or occur. Thus, it may be employed for example on plants or the soil.

Plants which may be treated include cotton and food crops, for example fruit trees and cereals, e.g. apples, pears, apricots, citrus fruits, maize, wheat, barley, beans, sugar beet, potatoes, carrots, or greenhouse crops, e.g. peppers, tomatoes, cucumbers, melons or strawberries.

In their various applications the compounds of formula I may be used at various rates: thus for example for the treatment of plants for the control of pests on plants the compounds are suitably applied at a rate of about 10–1000 g per hectare or at a concentration of 1 to 2000 ppm as appropriate, e.g. 100 to 1000 ppm, and preferably 50–300 g per hectare. Normally the compounds will be applied to the foliage of plants, but systemic activity may also observed when applied to the soil around the base of the plants.

The following Examples are given merely to illustrate the present invention. The temperatures given therein are in °C. and parts and percentages are by weight.

EXAMPLE 1

Isopropyl [3-(3-n-propyl-1,2,4-thiadiazol-5-yloxy)phenyl]-carbamate (a) 3-n-Propyl-5-(3-aminophenoxy)-1,2,4-thiadiazole A solution of 32.7 g of 3-aminophenol in 700 ml dimethylformamide was stirred and treated slowly with 9 g sodium hydride (80%), and was then heated to 50°20 C. A solution of 48.9 g of 3-n-propyl-5-chloro-1,2,4-thiadiazole in 150 ml dimethylformamide was then added dropwise, and the mixture was heated to 80° C. with stirring for 5 hours. Three liters of water were added and stirred for ½ hour, following which the product was extracted into diethyl ether (approximately 1 liter for 4 washings). After drying overnight over magnesium sulphate, the solution was filtered and evaporated, and 5% aqueous hydrochloric acid was added to form the hyrochloride salt. The aqueous solution of the salt was then extracted with diethyl ether, and sodium bicarbonate was added to the aqueous phase to pH 8. After further extraction into diethyl ether, and chromoatography, the desired product was obtained as an oil.

(b) 3-n-Propyl-5-(3-isocyanatophenoxy)-1,2,4-thiadiazole

Phosgene was passed for 1½ hours into 650 ml of toluene to form a saturated solution. To this was added 15.7 g of the product of stage (a), and the mixture was stirred and heated to reflux for 1 hour. The solvent was then evaporated to yield 13.4 g of the desired product.

(c) Isopropyl [3-(3-n-propyl-1,2,4-thiadiazol-5-yloxy)phenyl]carbamate

The product of stage (b) (4.17 g) was refluxed for 2½ hours with 400 ml of isopropanol. On evaporation of the solvent and recrystallisation from petroleum ether, the desired product was obtained in a yield of 57%, mp. 64° C.

EXAMPLES 2-12

The following compounds of formula I where $R^2$ is hydrogen, Y is oxygen and the carbamate group is in the 3-position on the phenyl ring were prepared by methods analogous to those of Example 1

| No. | R1 | R | M. Pt. |
| --- | --- | --- | --- |
| 2 | methyl | methyl | 117–119 |
| 3 | methyl | isopropyl | 69–71 |
| 4 | ethyl | isopropyl | 87–89 |
| 5 | ethyl | α-isopropylbenzyl | 93–95 |
| 6 | n-propyl | ethyl | 52–53 |
| 7 | n-propyl | n-propyl | 56 |
| 8 | n-propyl | n-butyl | 43 |
| 9 | n-propyl | isobutyl | 92–94 |
| 10 | n-propyl | t-butyl | 105–106 |
| 11 | n-propyl | phenyl | 115 |
| 12 | n-propyl | α-isopropylbenzyl | 99–101 |
| 13 | isopropyl | isopropyl | 74–76 |
| 14 | isopropyl | α-isopropylbenzyl | 87–89 |

-continued

| No. | R1 | R | M. Pt. |
| --- | --- | --- | --- |
| 15 | phenyl | isopropyl | 105 |
| 16 | phenyl | t-butyl | oil |
| 17 | n-propyl | 1-methylheptyl | oil |
| 18 | n-propyl | α-methylbenzyl | oil |
| 19 | n-propyl | sec-butyl | 86–88 |
| 20 | isopropyl | 1,1-dimethylpropargyl | 90–92 |

EXAMPLES 21-24

The following compounds of formula I where $R^2$ is hydrogen, Y is oxygen, and the carbamate group is in the 4-position on the phenyl ring, were prepared by methods analogous to that of Example 1:

| No. | R1 | R | M. Pt. |
| --- | --- | --- | --- |
| 21 | n-propyl | isopropyl | 73–74 |
| 22 | isopropyl | isopropyl | 64–66 |
| 23 | ethylthio | isopropyl | 117–119 |
| 24 | ethylthio | t-butyl | 97–99 |

EXAMPLE 25

The following compound of formula I where $R^2$ is hydrogen, Y is sulphur, and the carbamate group is in the 3-position on the phenyl ring, was prepared by a method analogous to that of Example 1:

| No | R1 | R | M. Pt. |
| --- | --- | --- | --- |
| 25 | n-propyl | isopropyl | oil |

EXAMPLE 26

Isopropyl [3-(3-n-propyl-1,2,4-thiadiazol-5-yloxy)phenyl]carbamate (alternative procedure)

(a) Isopropyl 3-hydroxyphenylcarbamate

A mixture of 3-aminophenol (109 g), magnesium oxide (25 g), water (350 ml) and ethyl acetate (100 ml) was stirred vigorously at room temperature while isopropyl chloroformate (123 g) was added slowly. An ice bath was employed to ensure that the temperature did not exceed 30° C. After stirring for one hour at room temperature, the mixture was filtered to remove insoluble particles. These were washed thoroughly with ether, then the filtrates were combined, then separated, and the organic layers were dried over magnesium sulphate. Evaporation under reduced pressure gave a viscous, pale yellow oil which was crystallised from toluene to give 162.7 g of desired product, mp 75°–77° C.

(b) Isopropyl [3-(3-n-propyl-1,2,4-thiadiazol-5-yloxy)phenyl]carbamate

A solution of the product of stage (a) (13.0 g) and 3-n-propyl-5-chloro-1,2,4-thiadiazole (10.2g) in tetrahydrofuran (350 ml), dried over a molecular sieve, was treated with sodium hydride (80%, 2.0 g), and was stirred and refluxed for 2 hours. It was then cooled to room temperature and was poured carefully into water (1 liter). After half an hour the ether extracts were separated, washed with water, and dried over sodium sulphate. The solvent was removed to give a pale yellow oil which was recrystallised from 60°–80° petrol to yield 14.2 g of desired product as a white solid, mp 63°–66°.

EXAMPLE 27

A 40% suspension concentrate formulation of the compound of Example 1 was prepared by blending the following ingredients:

|  | % w/w |
| --- | --- |
| Compound of Example 1 | 40 |
| Polyfon H (sodium salt of sulphonated Kraft lignin - Westvaco Corp.) | 2 |
| Pluronic P75 (ethylene oxide/ propylene oxide block copolymer) | 3 |
| Xanthan Gum | 0.2 |
| Formaldehyde | 0.2 |
| Water | q.s. |

Analogous 40% formulations were also prepared containing each of the compounds of Examples 2 to 25, as were analogous formulations respectively containing 0.5, 5, 10, 20, 50 and 85% by weight of the compound of Example 1 with corresponding changes in the amount of water employed.

EXAMPLE A

Discs (2 cm diameter) were cut from the lamina of the first true leaves of dwarf French bean plants, *Phaseolus vulgaris*. The discs were placed on moist 3 cm wide strips of filter paper, and 10–15 adult female mites (*Tetranychus cinnabarinus*) were placed on each disc. These were allowed to lay eggs for a period of 24 hours, and were then removed. The discs were then dipped into solutions of the compounds of the Examples listed below at various concentrations prepared by dissolving the appropriate quantity of the compound in 2 ml acetone plus 5% Atlox 1025A wetting agent and diluting the solution with water containing Synperonic N wetting agent so as to give an aqueous formulation containing 0.5 ml/liter Synperonic N, 20 ml/liter acetone and 1ml/liter Atlox 1025A.

Two replicates were used per treatment and the number of eggs hatching within 8 days was assessed.

The results below show the lowest rate tested at which the compounds enumerated killed at least 75% of the eggs.

| Compound Ex. No. | Rate (ppm) |
| --- | --- |
| 1 | 1 |
| 4 | 64 |
| 6 | 26 |
| 7 | 10 |
| 8 | 1.6 |
| 9 | 10 |
| 10 | 0.64 |
| 11 | 1.6 |
| 12 | 1.6 |
| 13 | 4 |
| 14 | 26 |
| 16 | 160 |
| 17 | 4 |
| 18 | 26 |
| 19 | 4 |
| 20 | 64 |
| 21 | 160 |
| 23 | 64 |

We claim:

1. A thiadiazole of the formula:

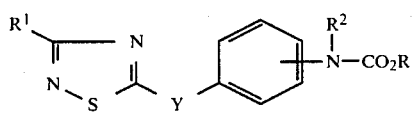

where: $R^1$ and $R^2$, which may be the same or different, are each hydrogen, optionally-halo or $C_{1-4}$ alkoxy substituted alkyl of 1 to 10 carbon atoms, or optionally-halo or $C_{1-4}$ alkoxy substituted phenyl, or $R^1$ is alkylthio of 1 to 6 carbon atoms; R is a halo or $C_{1-4}$ alkoxy substituted or unsubstituted alkyl group of 1 to 8 carbon atoms, a halo or $C_{1-4}$ alkoxy substituted or unsubstituted alkenyl or alkynyl group of 2 to 6 carbon atoms, a cycloalkyl group fo 3 to 6 carbon atoms, or a halo or $C_{1-4}$ alkoxy substituted or unsubstituted aryl group; Y is oxygen or sulphur; and the carbamate grouping is in the 3- or 4-position on the phenyl ring.

2. The thiadiazole according to claim 1 wherein $R^1$ is phenyl or alkyl of 1 to 6 carbon atoms.

3. The thiadiazole according to claims 1 or 2 wherein the carbamate group is attached to the phenyl ring in the 3-position.

4. The thiadiazole according to claim 1 wherein $R^1$ is ethyl, n-propyl, isopropyl, ethylthio or phenyl, $R^2$ is hydrogen, Y is oxygen, R is methyl, ethyl, n-propyl, isopropyl, n-butyl, isobutyl, sec-butyl, t-butyl, cyclopropyl, 1-methylheptyl, phenyl, α-methylbenzyl or α-isopropylbenzyl, and the carbamate group is attached to the phenyl ring in the 3-position.

5. A thinadiazole according to claim 1 wherein said thiadiazole is a [3-(3-n-Propyl-1,2,4-thiadiazol-5-yloxy)-phenyl]carbamate.

6. An acaricidal composition which comprises from 0.5 to 99% by weight of at least one thiadiazole according to claim 1 in association with a suitable carrier and/or surface active agent.

7. A method of combating acarids, their eggs or their larvae which comprises applying to a locus infested or liable to be infested therewith an effective amount of at least one thiadiazole according to claim 1.

8. The method of of claim 7 wherein $R^1$ is phenyl or alkyl of 1–6 carbon atoms.

9. The method of claim 7 wherein $R^1$ is ethyl, n-propyl, isopropyl, ethylthio or phenyl, $R^2$ is hydrogen, Y is oxygen, R is methyl, ethyl, n-propyl, isopropyl, n-butyl, isobutyl, sec-butyl, t-butyl, cyclopropyl, 1-methylheptyl, phenyl, α-methylbenzyl or α-isopropylbenzyl, and the carbamate group is attached to the phenyl ring in the 3-position.

10. The method of claim 7 wherein said thiadiazole is a [3-(3-n-propyl-1,2,4-thiadiazol-5-yloxy)phenyl]carbamate.

11. The composition of claim 6 wherein $R^1$ is phenyl or alkyl of 1–6 carbon atoms.

12. The composition of claim 6 wherein $R^1$ is ethyl, n-propyl, isopropyl, ethylthio or phenyl, $R^2$ is hydrogen, Y is oxygen, R is methyl, ethyl, n-propyl, isopropyl, n-butyl, isobutyl, sec-butyl, t-butyl, cyclopropyl, 1-methylheptyl, phenyl, α-methylbenzyl or α-isopropylbenzyl, and the carbamate group is attached to the phenyl ring in the 3-position.

13. The composition of claim 6 wherein said thiadiazol is a [3-(3-n-propyl-1,2,4-thiadiazole-5-yloxy)-phenyl]carbamate.

* * * * *